United States Patent
Mandler et al.

[11] Patent Number: 6,090,269
[45] Date of Patent: Jul. 18, 2000

[54] DETERMINATION OF CHROMIUM

[75] Inventors: Daniel Mandler; Iva Turyan, both of Jerusalem, Israel

[73] Assignee: Yissum Research Development Company of the Hebrew University of Jerusalem, Jerusalem, Israel

[21] Appl. No.: 09/011,058

[22] PCT Filed: Aug. 4, 1996

[86] PCT No.: PCT/IL96/00071

§ 371 Date: Mar. 30, 1998

§ 102(e) Date: Mar. 30, 1998

[87] PCT Pub. No.: WO97/06432

PCT Pub. Date: Feb. 20, 1997

[30] Foreign Application Priority Data

Aug. 4, 1995 [IL] Israel .................................. 114831

[51] Int. Cl.[7] .................................................. G01N 27/26
[52] U.S. Cl. .................................. 205/789.5; 205/794.5; 204/416
[58] Field of Search ............................. 204/416, 290 R, 204/291; 205/794.5, 789, 789.5; 427/2.11, 427

[56] References Cited

PUBLICATIONS

Xie et al. "Binding of cytochrome c with 4-pyridyl derivatives modified on gold electrodes", Electroanalysis (N.Y.) 1994, 6(7), 567–70), month unknown.
Andreu et al. ("Discreteness–of–Charge Effects at Molecular Films Containing Acid/Base groups", J. Phys. Chem, 1994, 98(48), 12753–8), month unknown.
Ure, A.M. et al., Ed., "Chemical Speciation in the Environment," Blackie Academic & Professional, pp. 363–365, (1995), month unknown.
Naghmush, A.M., et al., "Determination of Chromium in Different Oxidation States by Selective On–Line Preconcentration on Cellulose Sorbents and Flow–Injection Flame Atomic Absorption Spectrometry," Analytica Chimica Acta, vol. 288, pp. 247–257 (1994), month unknown.
Bauer, L., et al., "Addition of Thiourea to 2– and 4–Vinylpyridines," Journal of Organic Chemistry, vol. 26, pp. 82–85 (1961), month unknown.
Gui, J.Y., et al., "Surface Chemistry of Mercaptopyridines at Ag(111) Electrodes Studied by EELS, LEED, Auger Spectroscopy and Electrochemistry," J. Electronanal. Chem., vol. 292, pp. 245–262 (1990), month unknown.
Cox, J.A., et al., "Stripping Voltammetry of Chromium (VI) at a Poly(4–Vinylpyridine)–Coated Platinum Electrode," Analytica Chimica Acta, vol. 154, pp. 71–78 (1993), month unknown.
Elleouet, C., et al., "Determination of Trace Amounts of Chromium (VI) in Water by Electrochemical Methods," Analytica Chimica Acta, vol. 257, pp. 301–308 (1992), month unknown.

*Primary Examiner*—T. Tung
*Assistant Examiner*—Alex Noguerola
*Attorney, Agent, or Firm*—Foley & Lardner

[57] ABSTRACT

A highly sensitive assay for the determination of Cr(VI), in the presence of Cr(III) and in the presence of other cations by cyclic voltammetry. The determination is carried out with a gold or gold-plated electrode with a self-assembled monolayer of a pyridine derivative of the kind of 4-(2-ethanethiol) pyridine. Determinations can be affected at extremly low levels of the order of 1 ppt (part per trillion $10^{12}$).

9 Claims, 2 Drawing Sheets

DETERMINATION OF CHROMIUM

BACKGROUND OF THE INVENTION

Speciation is one of the major challenges present in analytical chemistry[1]. Of particular interest is metal speciation. For example, while Cr(III) is essential to our bodies and part of our daily diet, Cr(VI), i.e., chromate, is highly toxic to human causing gastrointestinal disorders, dermatitis, uncertain of skin and is a suspected carcinogenic agent. Thus, the determination of trace levels of Cr(VI), that are often below 1 ppb in natural waters and in biological fluids in the presence of relatively high concentrations of Cr(III) is of particular importance. Although the redox speciation of chromium has been accomplished by separate preconcentration of Cr(III) and Cr(VI) fractions using chelating resins, coprecipitation, ion chromatography and solent extraction, such procedures are obviously complicated[2]. Electroanalytical methods that are potentially sensitive for redox-specification have also been used to determine chromate[3]. Although Cr(VI) has been preconcentrated and determined on mercury and chemically modified solid electrodes, most of these interfaces exhibit moderate stability and selectivity when employed in natural samples.

SUMMARY OF THE INVENTION

According to the present invention there is provided an assay of extremely high sensitivity for the selective determination of Chromium (VI). There is also provided a selective electrode for such determinations based on the molecular design of the solid-liquid interface, using a self-assembled mono-layer. By structuring the solid liquid interface using a self-assembled monolayer (SAM), a highly sensitive electrode exhibiting speciation capabilities toward Cr(VI), was developed. Application of SAMs in electroanalytical chemistry presents a very attractive approach as a means of assembling selective electrodes. SAMs offer highly organised systems in which the solid-liquid interface can be pre-designed at the molecular level in order to acquire a modified surface with desired properties. For example, Rubinstein and co-workers[4] demonstrated that a mixed functionalised SAM recognised selectively $Cu^{2+}$ ions in the presence of other ions. More recently, the inventor presented a highly sensitive electrode for cadmium ions using ω-mercapto-carboxylic acid monolayers[5].

Thus, according to one aspect, the invention relates to a highly sensitive electrode for the selective quantitative detection and determination of Cr(VI) which comprises a gold electrode provided with a self-assembled monolayer (SAM) of a compound of the formula

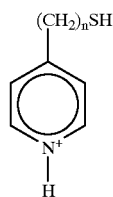

where n is zero or an integer from 1 to 18, preferred are electrodes where the SAM is one of positively charged 4-(2-ethanethiol) pyridinium. The invention also relates to a process for the preparation of Cr(VI)-selective gold electrodes which comprises polishing a gold surface of an electrode and contacting it with a dilute solution of a compound defined above, in the presence a mineral acid. A preferred mineral acid is sulfuric acid, and it is preferred the use of a solution of the pyridinium compound of about 5 mM and that of the sulfuric acid of about 0.1 M. Another aspect is a highly sensitive selective assay for Cr(VI), in the presence of Cr(III) and other cations, which is carried out by voltammetry using an electrode as defined above. Preferably there is used cyclic or square wave voltammetry. The assay is suitable for determinations in the range as low as the order of 1 ppt (part per trillion, $10^{12}$). There may be prepared a calibration curve of concentrations in the 1 ppt range is prepared, and actual results are read with the aid of such calibration curve. The can be carried out in the presence of Cr(III), $Cu^{2+}$, $Ag^+$, and $Fe^{3+}$, of a concentration greater than up to about $10^7$ as large than the Cr(VI) concentration, which ions do not interfere with the accuracy of the assay.

BRIEF DESCRIPTION OF THE DRAWINGS

The invention is illustrated in the following with reference to the enclosed Figures, in which:

FIG. 1B—Calibration curve for chromium (VI).

DETAILED DESCRIPTION OF THE INVENTION

Figure 1:
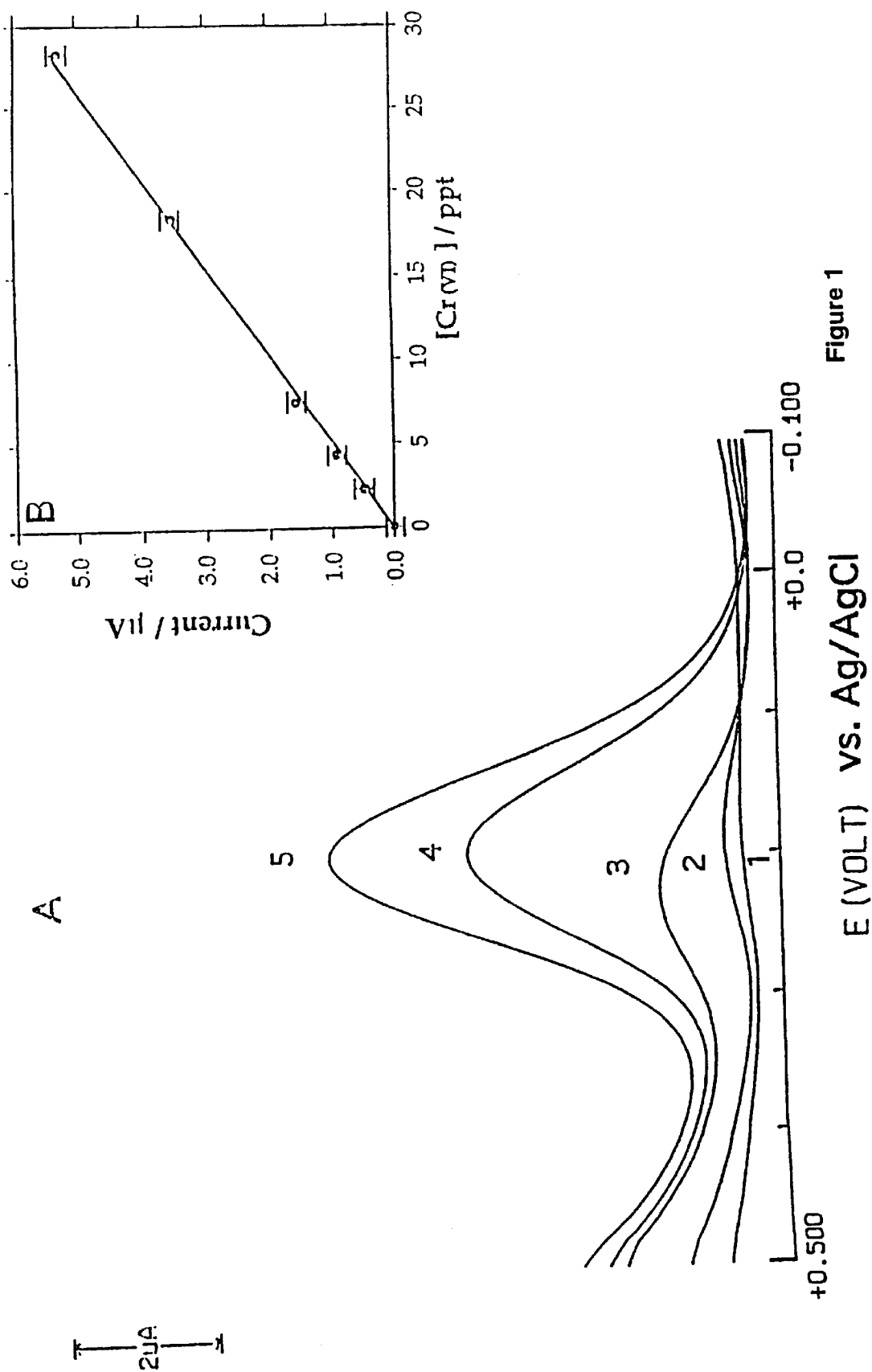
FIG. 1: A—Square wave voltammetry of a 4-(2-ethanethiol)pyridine modified gold electrode (scan rate 90 $mV.s^{-1}$) after a preconcentration step in solutions containing different concentrations of Cr(VI): (1)—0 ppt; (2)—1.60 ppt; (3)—4.30 ppt; (4)—18.36 ppt and (5)—28.28 ppt.

Electrodes of the invention for Cr(VI) are based on a positively charged 4-thiopyridinium or 4-(n-alkylthio) pyridinium, (I) monolayer on a gold surface. Pyridinium derivatives form strong and stable complexes with chromate, suggesting that a pyridinium-based SAM would effectively extract Cr(VI), while repelling cations, e.g., Cr(III). FIG. 1 shows a calibration curve for Cr(VI) using a gold electrode covered with a 4-(2-ethanethiol)pyridinium, $I_{n-2}$, monolayer[6] after optimizing all the parameters that control the performance of the electrode. The monolayer was assembled upon immersing a polished Au surface in 5 mM solution of thiol and 0.1 M $H_2SO_4$ for 10 min. Preconcentration of Cr(VI) was carried out in 0.15 M NaF (pH 4.5) solution for 5 min under open-circuit potential followed by the electrochemical determination in a chromium-free solution (0.15 M NaF, pH 7.8) by square wave voltammetry (FIG. 1). The remarkable detection limit of this electrode is lower than 1 ppt (part per trillion, $10^{12}$) with a relative standard deviation of 10% (5 ppt Cr(VI)),

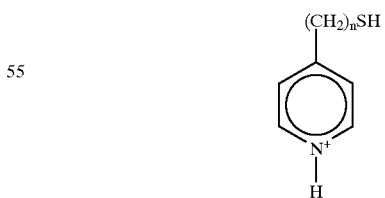

where n is an integer from 1 to 18,

The electroanalytical performance of such modified electrodes was studied in detail and reveals that other cations, e.g. $Cu^{2+}$, $Ag^+$ and $Fe^{3+}$ ($10^{-5}$ M of each), as well as anions such as $Cl^-$, $SCN^-$ and $MnO_4^-$ do not interfere with the determination of 8 ppt of Cr(VI). Moreover, the analysis of a sample consisting of 0.1 ppb of Cr)VI) was not affected at all by the presence of 1000 fold excess of Cr(III). Finally, the analysis of two samples consisting of 10.1 ppb of Cr(VI) and 5.05 ppb of Cr(VI) with 15 ppb of Cr(III) by graphite furnace atomic absorption (total chromium equals 10.1 ppb and 21.0 ppb, respectively) and by our electrode (10.03 ppb and 5.1 ppt of Cr(VI), respectively) were in excellent agreement.

Figure 2:
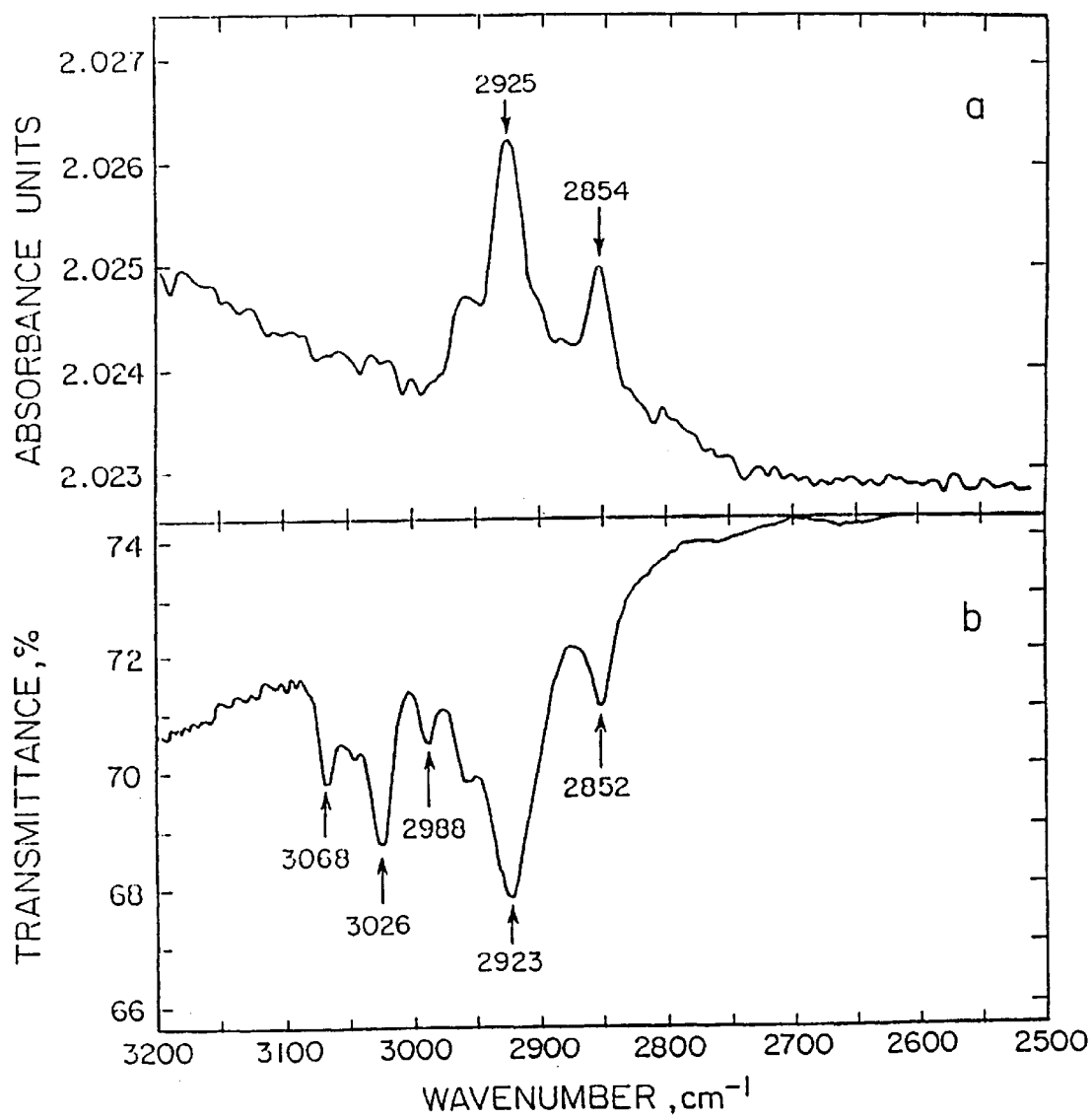
FIG. 2: Reflection-absorption FTIR spectrum of 4-(2-ethanethiol)pyridine adsorbed on gold (1) and transmission spectrum of liquid 4-(2-ethanethiol)pyridine (2).

The analytical performance of the electrode seems to be a result of the organisation of the interface as supported by its analysis using electrochemistry, FTIR, wettability and atomic force microscopy (AFM). Determination of the excess of surface coverage, r, by cyclic voltammetry of monolayers composed of 2 and 4-mercaptopyridine, as well as of $1_{n-2}$, shows that 4-substituted pyridines form more densely packed arrays. Specifically, $r_t$(4-mercaptopyridine)= $1.04 \pm 0.09$ nmol.cm$^{-2}$ as compared to $r_t$(2.mercaptopyridine)=$0.71 \pm 0.07$ nmol.cm$^{-2}$. It should be noted that the analytical signal recorded with a gold electrode modified with 2-mercaptopyridine was much smaller than the value that would have been obtained if the signal had been dependent only on the excess of surface coverage. This implies that the orientation of the pyridine ring plays a significant role in complexation. A more detailed characterization was accomplished by FTIR and AFM. FIG. 2 shows the IR spectra of the pure $1_{n-2}$ and its monolayer. These bands are assigned to the C-H stretching of the rings, whereas the bands at 2852 and 2923 cm$^{-1}$ correspond to the symmetric and assymetric alkyl C-H stretching, respectively. This indicates that the chain is oriented similarly to the chain of alkane thiols on gold, and the ring is oriented toward the solution. In this orientation the four C-H bands of the pyridine have only a minor dipole moment contribution normal to the surface, and therefore are not detected using a p-polarized incident beam with incident angle of 80°. AFM also provides evidence of the relatively high organization of the layer. Parallel rows with 0.42 nm spacing can be clearly seen in the unfiltered image. The AFM image as well as the IR results, match the structure (LEED pattern of (3 3x3 3)R30°) and orientation (perpendicular to the surface) which was suggested by Hubbard[7] for a 4-mercaptopyridine monolayer on Ag(111).

The high selectivity of the interface toward Cr(VI) cannot be attributed only to the positive charge of the pyridinium moiety as is indicated by the fact that a 2-aminoethanethio monolayer extracted Cr(VI) very poorly. The extraction of chromate was followed also by wettability and capacitive measurements. Clear changes in the advancing contact angles ($\Delta 0 = 12 \pm 3$) of aqueous buffered solutions on films of $I_{n-2}$ on gold, as well as in the differential capacity of the double layer ($\Delta C_{dl} = 11.3 \pm 1.8$ $\mu$F.cm$_{-2}$) were observed upon introducing chromate ions.

In conclusion, all these results suggest that the high sensitivity and selectivity toward Cr(VI) are governed by the chemical and physical structure of the monolayer. The ability to fine tune and probe in depth the interface structure by microscopic and macroscopic tools is crucial to designing highly sensitive and species-selective probes.

REFERENCES

1. Ure, A. M. & Davidson, C. M., Ed. *Chemical Speciation in the Environment*, Blackie Academic & Professional: Glasgow, 1995, p. 408.

2. Nahhmush, A. M., Pyrzynska, K. & Trojanowicz, M. *Anal. Chim.* Acta 288, 247–257 (1994).

3. For example: Boussemart, M., van den Berg, C. M. G. & Ghaddaf, M. *Anal. Chim.* Acta 262, 103–115 (1992)

4. Rubinstein, I., Steinberg, S., Tor, Y., Shanzer, A. & Sagiv, *J. Nature* 332, 426–429 (1988).

5. Turyan, I. & Mandler, D. *Anal. Chem.* 66, 58–63 (1994).

6. Bauer, L. & Gardella, L. A. Jr. *J. Org. Chem.* 26, 82–85 (1961).

7. Gui, J. Y., Lu, F., Stern, D. A. & Hubbard, A. T. *J. Electroanal. Chem.* 292, 245–262 (1990).

What is claimed is:

1. A sensitive electrode for the selective quantitative detection and determination of Cr(VI) characterized in that there can be assayed quantities as low as 1 ppt, which comprises a gold electrode provided with a self-assembled monolayer (SAM) of a compound of the formula

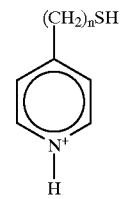

where n is an integer from 1 to 18.

2. An electrode according to claim 1, where the SAM is one of positively charged 4-(2-ethanethiol) pyridinium.

3. A process for the preparation of Cr(VI)-selective gold electrodes which comprises polishing a gold surface of an electrode and contacting it with a dilute solution of a compound defined in claim 1, in the presence a mineral acid.

4. A process according to claim 3, where the acid is sulfuric acid.

5. A process according to claim 4, where the solution of the pyridinium compound is 5 mM and that of the sulfuric acid is about 0.1 M.

6. A method for detecting and determining Cr(VI) in a solution comprising the steps of (a) immersing a gold electrode having a self assembled monolayer of a compound of the formula

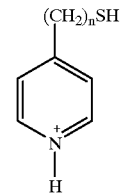

wherein n is zero or an integer from 1 to 18, in a solution comprising Cr(VI) and 0.15 M NaF(pH4.5), wherein the step of immersing is under open circuit potential; and b) analyzing the Cr(VI) by voltammetry.

7. A method according to claim 6 wherein the voltammetry method is square wave voltammetry.

8. A method according to claim 6 wherein said method can detect Cr(VI) in said solution at a concentration of as low as about 1 part per trillion.

9. A method according to claim 6 for detecting and determining Cr(VI) in a solution in the presence of Cr(III) and other ions.

* * * * *